(12) United States Patent
Vogt et al.

(10) Patent No.: US 11,490,941 B2
(45) Date of Patent: Nov. 8, 2022

(54) DEVICE FOR PROVIDING BONE CEMENT

(71) Applicant: Heraeus Medical GmbH, Wehrheim (DE)

(72) Inventors: Sebastian Vogt, Wehrheim (DE); Thomas Kluge, Wehrheim (DE)

(73) Assignee: Heraeus Medical GmbH, Wehrheim (DE)

(*) Notice: Subject to any disclaimer, the term of this patent is extended or adjusted under 35 U.S.C. 154(b) by 397 days.

(21) Appl. No.: 16/655,345

(22) Filed: Oct. 17, 2019

(65) Prior Publication Data
US 2020/0129216 A1  Apr. 30, 2020

(30) Foreign Application Priority Data

Oct. 25, 2018 (DE) .................. 10 2018 218 302.3
Oct. 25, 2018 (DE) .................. 10 2018 218 303.1

(51) Int. Cl.
*A61B 17/88* (2006.01)
*B01F 23/50* (2022.01)
(Continued)

(52) U.S. Cl.
CPC ...... *A61B 17/8833* (2013.01); *A61B 17/8822* (2013.01); *B01F 23/59* (2022.01);
(Continued)

(58) Field of Classification Search
CPC ........ A61B 17/8833; A61B 2017/8838; A61B 17/8827; A61B 17/8825; B01F 35/754251; B01F 33/50112; B01F 2101/20
See application file for complete search history.

(56) References Cited

U.S. PATENT DOCUMENTS 2,446,501 A   12/1944  Weber
2,591,046 A    4/1952  Brown
(Continued)

FOREIGN PATENT DOCUMENTS

CN     108421132     8/2018
DE       3640279     6/1987
(Continued)

OTHER PUBLICATIONS

Non-Final Office Action dated Jul. 29, 2021 in U.S. Appl. No. 16/705,881.
(Continued)

*Primary Examiner* — Matthew J Lawson
(74) *Attorney, Agent, or Firm* — Dicke, Billig & Czaja, PLLC

(57) ABSTRACT

One aspect relates to a device for providing a bone cement from two starting components, having a hollow cylinder-shaped first container, in which a monomer liquid as first starting component can be stored, a hollow cylinder-shaped second container comprising a container wall, a first internal space, and a second internal space, whereby a bone cement powder as second starting component can be stored in the first internal space, and whereby the monomer liquid can be conveyed into the second internal space, a fluid-conducting conveying means arranged between the first internal space and the second internal space, whereby the first container and the second container are axially connected to each other.

10 Claims, 8 Drawing Sheets

(51) Int. Cl.
*B01F 35/71* (2022.01)
*B01F 35/75* (2022.01)
*B01F 33/501* (2022.01)
*B01F 101/20* (2022.01)

(52) U.S. Cl.
CPC ...... *B01F 35/7131* (2022.01); *B01F 35/7161* (2022.01); *B01F 35/754251* (2022.01); *A61B 2017/8838* (2013.01); *B01F 33/50112* (2022.01); *B01F 2101/20* (2022.01)

(56) References Cited

U.S. PATENT DOCUMENTS

| | | | |
|---|---|---|---|
| 2,754,590 A | 7/1956 | Cohen | |
| 2,869,543 A | 1/1959 | Ratcliff et al. | |
| 3,028,052 A | 4/1962 | Archer | |
| 3,164,303 A | 1/1965 | Trautmann | |
| 3,464,412 A | 9/1969 | Schwartz | |
| 3,480,014 A | 11/1969 | Callahan | |
| 3,659,749 A * | 5/1972 | Schwartz | B01F 33/50112 222/386 |
| 3,684,136 A | 8/1972 | Baumann | |
| 3,739,947 A | 6/1973 | Baumann et al. | |
| 3,785,379 A * | 1/1974 | Cohen | A61M 5/31596 604/88 |
| 4,391,590 A | 7/1983 | Dougherty | |
| 4,648,532 A | 3/1987 | Green | |
| 4,671,263 A | 6/1987 | Draenert | |
| 4,758,096 A | 7/1988 | Gunnarsson | |
| 4,898,580 A | 2/1990 | Crowley | |
| 4,968,299 A | 11/1990 | Ahlstrand et al. | |
| 4,972,969 A | 11/1990 | Randklev | |
| 4,973,168 A | 11/1990 | Chan | |
| 5,026,283 A | 6/1991 | Osanai et al. | |
| 5,100,241 A | 3/1992 | Chan | |
| 5,344,232 A | 9/1994 | Nelson et al. | |
| 5,551,778 A | 9/1996 | Hauke et al. | |
| 5,586,821 A | 12/1996 | Bonitati et al. | |
| 5,588,745 A | 12/1996 | Tanaka et al. | |
| 5,624,184 A | 4/1997 | Chan | |
| 5,779,356 A | 7/1998 | Chan | |
| 5,971,953 A | 10/1999 | Bachynsky | |
| 5,997,544 A | 12/1999 | Nies et al. | |
| 6,017,349 A | 1/2000 | Heller et al. | |
| 6,033,105 A | 3/2000 | Barker et al. | |
| 6,120,174 A | 9/2000 | Hoag et al. | |
| 6,386,872 B1 | 5/2002 | Mukasa et al. | |
| 6,544,233 B1 | 4/2003 | Fukui et al. | |
| 6,709,149 B1 | 3/2004 | Tepic | |
| 6,869,284 B2 | 3/2005 | Aoyagi et al. | |
| 6,935,541 B1 | 8/2005 | Campbell et al. | |
| 7,073,936 B1 * | 7/2006 | Jonsson | B01F 35/718 366/139 |
| 8,128,276 B2 | 3/2012 | Axelsson et al. | |
| 8,690,419 B2 | 4/2014 | Faccioli et al. | |
| 8,747,866 B2 | 6/2014 | Vogt et al. | |
| 8,757,866 B2 | 6/2014 | Vogt et al. | |
| 8,968,000 B2 | 3/2015 | Leiner et al. | |
| 9,247,979 B2 | 2/2016 | Faccioli et al. | |
| 9,326,829 B2 | 5/2016 | Kojima et al. | |
| 9,775,690 B2 | 10/2017 | Cheetham | |
| 2003/0012079 A1 * | 1/2003 | Coffeen | A61B 17/8822 366/195 |
| 2004/0074927 A1 | 4/2004 | Lafond | |
| 2004/0122359 A1 * | 6/2004 | Wenz | B01F 35/713 604/82 |
| 2005/0128868 A1 * | 6/2005 | Vries | B01F 35/754251 366/139 |
| 2005/0222538 A1 | 10/2005 | Embry et al. | |
| 2006/0274601 A1 * | 12/2006 | Seaton | B01F 31/441 366/139 |
| 2012/0155214 A1 * | 6/2012 | Faccioli | A61B 17/8822 366/130 |
| 2013/0090596 A1 * | 4/2013 | Asai | A61M 5/315 604/89 |
| 2014/0110356 A1 * | 4/2014 | McKay | G06F 16/972 210/402 |
| 2014/0192611 A1 | 7/2014 | Sasaki et al. | |
| 2014/0254303 A1 | 9/2014 | McArthur et al. | |
| 2014/0269147 A1 * | 9/2014 | Click | B01F 35/754251 366/98 |
| 2015/0329339 A1 * | 11/2015 | Oberli | A61B 17/8833 225/93 |
| 2016/0045283 A1 * | 2/2016 | Boehm | A61C 5/66 433/90 |
| 2017/0252715 A1 | 9/2017 | Vogt et al. | |
| 2018/0132917 A1 | 5/2018 | Vogt et al. | |
| 2018/0132919 A1 | 5/2018 | Vogt et al. | |
| 2018/0256233 A1 | 9/2018 | Vogt et al. | |
| 2018/0289406 A1 | 10/2018 | Vogt et al. | |
| 2018/0310974 A1 | 11/2018 | Vogt et al. | |
| 2018/0333176 A1 | 11/2018 | Vogt et al. | |
| 2019/0216516 A1 | 7/2019 | Vogt et al. | |
| 2020/0129215 A1 | 4/2020 | Vogt | |
| 2020/0179023 A1 | 6/2020 | Vogt | |
| 2020/0179024 A1 | 6/2020 | Vogt | |

FOREIGN PATENT DOCUMENTS

| | | |
|---|---|---|
| DE | 69812726 | 2/2004 |
| DE | 20 2005 010 206 | 9/2005 |
| DE | 10 2009 031 178 | 9/2010 |
| DE | 102009031178 | 9/2010 |
| DE | 102016121607 | 5/2018 |
| DE | 10 2018 101 041 | 7/2019 |
| EP | 0 692 229 | 1/1996 |
| EP | 0692229 | 1/1996 |
| EP | 0 796 653 | 9/1997 |
| EP | 0796653 | 9/1997 |
| EP | 1 005 901 | 6/2000 |
| EP | 1005901 | 6/2000 |
| EP | 1 016 452 | 7/2000 |
| EP | 1 020 167 | 7/2000 |
| EP | 1016452 | 7/2000 |
| EP | 1020167 | 7/2000 |
| EP | 1093826 | 4/2001 |
| EP | 1 886 647 | 2/2008 |
| EP | 1886647 | 2/2008 |
| EP | 1883379 | 9/2013 |
| EP | 3320870 | 5/2018 |
| JP | 2011-067265 | 4/2011 |
| WO | 94/26403 | 11/1994 |
| WO | 99/67015 | 12/1999 |
| WO | 00/35506 | 6/2000 |
| WO | 2006/123205 | 11/2006 |
| WO | 2011/089480 | 7/2011 |
| WO | 2012/115022 | 8/2012 |

OTHER PUBLICATIONS

Non-Final Office Action dated Aug. 10, 2021 in U.S. Appl. No. 16/655,610.
Charnley, J., "Anchorage of the Femoral Head Prosthesis of the Shaft of the Femur," The Journal of Bone and Joint Surgery, 42 B, No. 1, pp. 28-30 (Feb. 1960).
Kuhn, Klaus-Dieter, "Bone Cements," Springer-Verlag, pp. 9 (2000).
Notice of Allowance dated Jun. 3, 2022 in U.S. Appl. No. 16/705,969.

* cited by examiner

DEVICE FOR PROVIDING BONE CEMENT

CROSS-REFERENCE TO RELATED APPLICATIONS

This Utility Patent Application claims priority to German Patent Application No. 10 2018 218 302.3, filed Oct. 25, 2018 and German Patent Application No. 10 2018 218 303.1, filed Oct. 25, 2018, both of which are incorporated herein by reference. This Utility Patent Application is related to U.S. Ser. No. 16/655,610 filed Oct. 17, 2019.

TECHNICAL FIELD

One embodiment relates to a device for providing a bone cement from two starting components. One embodiment relates to a method for providing a bone cement from two starting components

BACKGROUND

Considerable effort is being undertaken to devise devices and methods for the provision of bone cement by means of which the bone cement thereof can be provided easily, safely, and rapidly. One aspect of the provision of bone cement is the prevention of air inclusions in the bone cement. To prevent these, a large number of vacuum cementing systems have been described of which the following shall be listed for exemplary purposes: U.S. Pat. Nos. 6,033,105 A, 5,624,184 A, 4,671,263 A, 4,973,168 A, 5,100, 241 A, WO 99/67015 A1, EP 1020167 A2, U.S. Pat. No. 5,586,821 A, EP 1016452 A2, DE 3640279 A1, WO 94/26403 A1, EP 1005901 A2, EP 1886647 A1, U.S. Pat. No. 5,344,232 A.

There is a desire in the market to simplify the provision of bone cement. One advanced development is the development of cementing systems, in which both starting components are stored in separate areas of the mixing systems and are mixed with each other in the cement system only immediately prior to the cementing application. The closed, so-called full-prepacked systems, are specified in the following specifications: EP 0692229 A1, DE 10 2009 031 178 B3, U.S. Pat. Nos. 5,997,544 A, 6,709,149 B1, DE 698 12 726 T2, EP 0796653 A2, U.S. Pat. No. 5,588,745 A.

DE 10 2016 121 607 A1 describes a full-prepack system, whereby the monomer liquid-filled container is stored axially behind the bone cement. It is disadvantageous that the monomer liquid-filled container needs to be destroyed completely in the course of the mixing of the starting components. It has also been evident to be a disadvantage that the input of force, in order to mix the starting components and later on to dispense the mixed bone cement, always acts on the fragments of the destroyed container as well. This leads to an increased physical effort for the user and to jerky and uncontrollable motions both during the destruction of the containers and during the mixing and later dispensing of the mixed cement. Both of these significantly complicate the applicability of the full-prepack system, in particular in the course of time-critical operation conditions. It has been evident to be just as disadvantageous that the destroyed container complicates the use of the full pre-packed system. This is related, for example, to fragments of the container that retain monomer liquid which is then not available for production of the bone cement. Another disadvantage arises from the fragments of the container wedging inside the mixing and dispensing device. Another disadvantage is the hazard potential of the fragments both for the user and for the patients.

SUMMARY

One embodiment relates to a device for providing a bone cement from two starting components, comprising a hollow cylinder-shaped first container, in which a monomer liquid as first starting component can be stored, a hollow cylinder-shaped second container comprising a container wall, a first internal space, and a second internal space, whereby a bone cement powder as second starting component can be stored in the first internal space, and whereby the monomer liquid can be conveyed into the second internal space, a fluid-conducting conveying means arranged between the first internal space and the second internal space, whereby the first container and the second container are axially connected to each other. One embodiment also relates to a method for providing a bone cement from two starting components by means of a device comprising a hollow cylinder-shaped first container, in which a monomer liquid as a first starting component is stored in a vessel, a hollow cylinder-shaped second container comprising a container wall, a first internal space, and a second internal space, whereby a bone cement powder as second starting component is stored in the first internal space, whereby the monomer liquid can be conveyed into the second internal space, a fluid-conducting conveying means arranged between the first internal space and the second internal space, and whereby the first container and the second container are axially connected to each other.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

DETAILED DESCRIPTION

Figure 1:
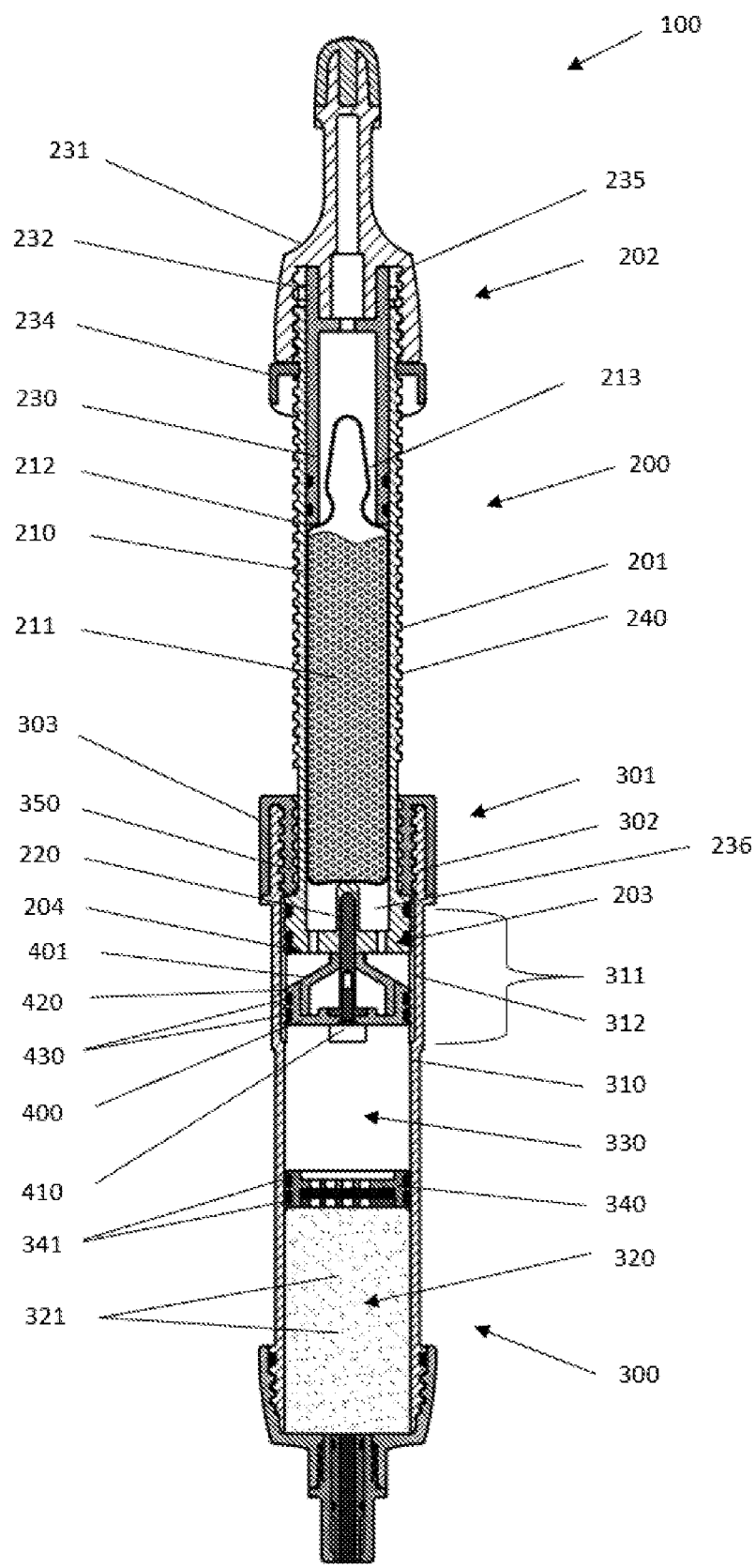
FIG. 1 illustrates a schematic drawing of a cross-section of a device for the provision of a bone cement from two starting components

In the following Detailed Description, reference is made to the accompanying drawings, which form a part hereof, and in which is illustrated by way of illustration specific embodiments in which one embodiments may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present embodiments. The following detailed description, therefore, is not to be taken in a limiting sense, and the scope of the present embodiments are defined by the appended claims.

It is to be understood that the features of the various exemplary embodiments described herein may be combined with each other, unless specifically noted otherwise.

It is an object of at least one present embodiment to overcome, at least in part, one or more of the disadvantages resulting according to the prior art.

Specifically, one embodiment is based on the goal to provide devices for the provision of a bone cement from two starting components, which require a lesser exertion of force by the user than previous cementing systems, which, in addition, are easy to handle and safe to use. It is another goal to minimise the infection hazard for the patient. The devices should be well-suited for storing the two starting components separate from each other. It should be possible to combine the two starting components in the closed device within a few seconds. The device is to provide the bone cement without any mechanical mixing of the starting components Moreover, the device is to be designed appropriately such that the user does not have to perform any assembly steps. The device is to be capable of providing the bone cement without a vacuum being applied from outside. The device is to be capable of dispensing the bone cement thus provided. The device is to be capable of dispensing the bone cement thus provided without any conversion measures. The device is to provide and dispense the bone cement without conversion measures and without external apparatuses, such as, for example, hoses, vacuum sources or extrusion devices. The device shall be operated by as few working steps as possible in order to minimise user-related error sources.

It is another object of at least one embodiment to provide a method by means of which a bone cement made of two starting components can be provided, by means of which at least a part of the objects described above can be solved at least in part.

The features of the independent claims make a contribution to meeting, at least partially, at least one of the objects specified above. The dependent claims are preferred in one embodiment that contribute to meeting, at least partially, at least one of the objects.

[1] Device for the provision of a bone cement from two starting components, comprising
  a hollow cylinder-shaped first container, in which a monomer liquid as first starting component can be stored;
  a hollow cylinder-shaped second container comprising a container wall, a first internal space, and a second internal space;
  whereby a bone cement powder as second starting component can be stored in the first internal space; and
  whereby the monomer liquid can be conveyed into the second internal space;
  a fluid-conducting conveying means arranged between the first internal space and the second internal space;
  whereby the first container and the second container are axially connected to each other;
  characterized by
  a dispensing plunger that can be axially shifted in the second container and is arranged between the first container and the second internal space;
  whereby the dispensing plunger appropriately acts in concert with the container wall such that,
  in a first position of the dispensing plunger, the first container and the second internal space are connected in monomer liquid-conducting manner; and,
  in a second position of the dispensing plunger, the first container and the second internal space are not connected in monomer liquid-conducting manner.

[2] Device according to embodiment 1, characterized in that the container wall includes a first subsection with at least one recess and a second subsection that is designed to be recess-free.

[3] Device according to embodiment 2, characterized in that the dispensing plunger, in the first position, is adjacent to the first subsection in appropriate manner such that the monomer liquid can flow about the dispensing plunger via the at least one recess.

[4] Device according to embodiment 2 or 3, characterized in that the dispensing plunger, in the second position, is adjacent to the second subsection in appropriate manner such that the monomer liquid cannot flow about the dispensing plunger.

[5] Device according to any one of the preceding embodiments, characterized in that the dispensing plunger is cambered.

[6] Device according to any one of the preceding embodiments, characterized in that the first container and the dispensing plunger are designed to be a single part.

[7] Device according to any one of the preceding embodiments, characterized in that the first container contains a vessel with the monomer liquid.

[8] Device according to embodiment 7, characterized in that the first container includes an opening device for the vessel.

[9] Device according to embodiment 7 or 8, characterized in that the vessel is a glass ampoule.

[10] Device according to embodiment 9, characterized in that the opening device is a puncturing mandrel.

[11] Device according to any one of the embodiments 8 to 10, characterized in that the first container includes an axially shiftable conveying plunger, designed appropriately such that the vessel can be conveyed onto the opening device by the conveying plunger.

[12] Device according to any one of the preceding embodiments, characterized in that the first container can be inserted axially, at least in part, into the second container in appropriate manner such that the dispensing plunger can be moved over the length of the second internal space and at least a part of the length of the first internal space.

[13] Device according to any one of the preceding embodiments, characterized in that the first container includes an external thread and the second container includes an internal thread, whereby the external thread and the internal thread are connected or can be connected to each other in form-fitting and/or force-locking manner.

[14] Method for the provision of a bone cement from two starting components by means of a device comprising a hollow cylinder-shaped first container, in which a monomer liquid as first starting component is stored in a vessel;

a hollow cylinder-shaped second container comprising a container wall, a first internal space, and a second internal space;

whereby a bone cement powder as second starting component is stored in the first internal space;

whereby the monomer liquid can be conveyed into the second internal space;

a fluid-conducting conveying means arranged between the first internal space and the second internal space, and whereby the first container and the second container are axially connected to each other, at least comprising the following sequential sub-steps:

a. opening the vessel;
b. the monomer liquid flowing about the dispensing plunger into the second internal space;
c. conveying the monomer liquid from the second internal space into the first internal space through a first shift of the first container into the second container;
d. production of the bone cement from bone cement powder and monomer liquid.

[15] Method according to embodiment 14, characterized in that the bone cement is dispensed from the device in a sub-step e) through a second shift of the first container into the second container.

Ranges specified in the present description include the values specified as the limits. A specification of "in the range of X to Y" with regards to a parameter A therefore means that A can assume values X, Y, and values between X and Y. Accordingly, ranges of a parameter A limited on one side in the way of "up to Y" include values equal to Y and less than Y.

A first subject matter of one embodiment relates to a device for the provision of a bone cement from two starting components, comprising a hollow cylinder-shaped first container, in which a monomer liquid as first starting component can be stored, a hollow cylinder-shaped second container comprising a container wall, a first internal space, and a second internal space, whereby a bone cement powder as second starting component can be stored in the first internal space, and whereby the monomer liquid can be conveyed into the second internal space, a fluid-conducting conveying means arranged between the first internal space and the second internal space, whereby the first container and the second container are axially connected to each other, characterized by a dispensing plunger that can be axially shifted in the second container and is arranged between the first container and the second internal space; whereby the dispensing plunger appropriately acts in concert with the container wall such that, in a first position of the dispensing plunger, the first container and the second internal space are connected in monomer liquid-conducting manner; and, in a second position of the dispensing plunger, the first container and the second internal space are not connected in monomer liquid-conducting manner. Arranging the dispensing plunger between the first container and the second internal space allows for a direct action of force, not on the vessel, but on the monomer liquid that is conveyed into the second internal space through an axial shift of the dispensing plunger. As a result, the vessel does not need to be destroyed completely after the vessel is opened and the monomer liquid flows out. Consequently, the user has to expend less force and the conveyance of the monomer liquid into the first internal space proceeds well-controlled, since no fragments of the vessel are situated in the displacement pathway of the dispensing plunger. Since the vessel needs to be opened only in a spot, but does not have to be destroyed completely, there is a lower risk of fragments of the vessel becoming wedged during the use of the device. Likewise, the injury risk from fragments is lowered both for the patient and the user.

As a result of the spatial positioning of the dispensing plunger between the first container and the second internal space, the dispensing plunger, in concert with the container wall, needs to be designed initially permeable to gases and liquids for the monomer liquid to be able to access the second internal space. Subsequently, the dispensing plunger needs to be designed impermeable to liquids and solids since, unless this is the case, the monomer liquid cannot be conveyed from the second internal space into the first internal space. According to one embodiment, the dispensing plunger undergoes a transformation from being permeable to gases and liquids to being impermeable to liquids and solids in the course of the use of the device. According to one embodiment, a position of the dispensing plunger shall be understood to be a state of the dispensing plunger or a spatial arrangement of the dispensing plunger in the second container.

In an embodiment, the dispensing plunger, in the first position, includes at least one opening that permits the exchange of gases and liquids between the first container and the second internal space. Accordingly, the at least one opening is closed to liquid and solid matter in the second position of the dispensing plunger. For example, the dispensing plunger in the first position can comprise at least one opening that can be closed by rotating the dispensing plunger about the longitudinal axis of the dispensing plunger into the second position such that no further exchange takes place.

The device according to one embodiment includes hollow cylinder-shaped containers. A hollow cylinder-shaped container shall be understood to be a tubular container that includes an internal space and a container wall that surrounds the internal space. The hollow cylinder-shaped container contains a cross-section perpendicular to a longitudinal axis. One embodiment can provide a container to comprise more than one internal space. For example, a container can comprise two internal spaces, three internal spaces or four internal spaces. If a container includes more than one internal space, the internal spaces are preferred, according to one embodiment, to be separated from each other by means of a separating wall or a conveying means. According to one embodiment, the cross-section of the containers can take any shape. For example, the cross-section can be designed to be oval, square, pentagonal, hexagonal, irregular or circular.

The hollow cylinder-shaped container is preferred to comprise a cylindrical geometry with a rotationally symmetrical axis with a round cross-section. The geometry allows for good handling by the user and the absence of edges reduces the risk of moving parts becoming wedged inside the device. According to one embodiment, the containers can consist of a broad range of materials or combinations of materials. For example, the device can consist of plastic material. In one embodiment, the plastic material is a transparent plastic material as this allows the user to control by eye the proper function of the device during a use of the device.

The device according to one embodiment is characterized in that the first hollow cylinder-shaped container and the second hollow cylinder-shaped container are axially connected to each other. A connection is axial if the two longitudinal axes of the hollow cylinder-shaped containers extend essentially in the same direction and in one embodiment essentially superimpose. According to one embodiment, upon axial connection, the cross-sectional planes of the connected containers are essentially parallel to each other.

The term "essentially" shall be understood to mean that a mathematically exact interpretation of terms such as "superimposition", "perpendicular" or "parallelism" can never be evident exactly, but only within certain error tolerances of production technology for real conditions and production technologies. For example, the two longitudinal axes of the containers can be at a distance from each other of up to 5 mm, in particular of up to 2 mm or have an outside angle of up to 5°, in particular of up to 2°.

Another embodiment of the device is characterized in that the container wall includes a first subsection with at least one recess and a second subsection that is designed to be recess-free. According to one embodiment, a subsection of the container wall shall be understood to be a section of the container wall extending in axial direction, whereby the section includes the full radial circumference of the container wall. A recess shall be understood to be a reduction of the thickness of the container wall, whereby the reduction is designed on an internal side of the container wall. The recesses can possess any cross-sectional shape such as around, oval, triangular, square or irregular. The recesses extend essentially axially in the container wall. In this context, the extension can be parallel to the longitudinal axis of the container or be at an angle of less than 90°. The recesses can possess different widths perpendicular to the axial extension. In an embodiment, the width of the recess extends over the entire circumference of the container. In another embodiment, the recesses have a width between 0.2 mm to 3 cm, in particular between 0.5 mm to 1.5 mm. The recesses can have different depths. For example, the recesses have a depth of 0.01 mm to 2 mm, in particular of 0.1 mm to 1 mm. Depth and width of the recesses are selected appropriately such that the structural integrity of the container is not adversely affected. For example, the recesses can have a depth of 0.5 mm and a width of 1.5 cm.

In this context, the first subsection can possess one or more than one recess. For example, the first subsection can possess four recesses distributed evenly on the container wall with a centre angle of 90° between two recesses.

Another embodiment of the device is characterized in that the dispensing plunger, in the first position, is adjacent appropriately to the first subsection such that the monomer liquid can flow about the dispensing plunger via the at least one recess. According to one embodiment, the dispensing plunger in the first position is at the spatial height of the first subsection. The recesses have a longer axial extension than an external surface of the dispensing plunger that is adjacent to the first subsection such that the monomer liquid can flow from the first container around the external surface of the dispensing plunger into the second internal space. It is an advantage of the embodiment that gravity can be utilised to convey the monomer liquid from the first container into the second internal space which renders additional apparatuses, such as, for example, pumps, superfluous. For this purpose, the opened vessel is held such that the first container is situated at a higher spatial level than the second container. Moreover, the design of the device according to one embodiment minimises possible error sources and user errors since it is only necessary to open the vessel and to hold the device according to the orientation described above in order to convey the monomer liquid into the second internal space. No additional conversion measure or additional working step, such as, for example, the actuation of a lever, is required.

Another embodiment of the device is characterized in that the dispensing plunger, in the second position, is adjacent to the first subsection in appropriate manner such that the monomer liquid can not flow about the dispensing plunger. According to one embodiment, the dispensing plunger in the second position is at the spatial height of the second subsection in appropriate manner such that dispensing plunger and container wall do not permit any exchange of liquid and solid matter between the first container and the second internal space. In this context, the external surface of the dispensing plunger can be directly adjacent to the container wall of the second subsection or the external surface of the dispensing plunger can comprise one or more sealing rings adjacent to the container wall. In one embodiment, the external surface includes one or more sealing rings. The sealing rings in one embodiment encompass the entire external surface of the dispensing plunger and are attached perpendicular to the longitudinal axis of the device. The sealing rings consist of a flexible plastic material, designed appropriately such that the sealing rings, firstly, ensure good sealing of the dispensing plunger in the second position between first container and second internal space, and, secondly, render the dispensing plunger not too difficult to axially shift for the user. A compromise between these two properties has been found through the use of two sealing rings. The inventive embodiment of the device allows a reduction of error sources to be attained since the axial shift of the dispensing plunger for conveying the monomer liquid from the second internal space into the first internal space automatically closes the second internal space such as to be non-fluid-conducting with respect to the first container. No additional conversion measure or additional working step, such as, for example, the actuation of a lever, is required.

Another embodiment of the device is characterized in that the dispensing plunger is cambered. According to one embodiment, the dispensing plunger can take a variety of shapes on a top side that faces the first container. For example, the top side can be flat or cambered. According to one embodiment, a cambered dispensing plunger shall be understood to be an arched dispensing plunger, whereby the arch is most pronounced in the area of the rotary axis of the dispensing plunger and decreases in outward direction. In one embodiment, the top side is cambered such that the monomer liquid flowing out of the opened vessel is conducted in the direction of the recesses in the container wall of the second container. Accordingly, a cambered dispensing plunger reduces the risk of the conveying of the monomer liquid into the second internal space being incomplete.

Another embodiment of the device is characterized in that the first container and the dispensing plunger are designed to be a single part. According to one embodiment, the term "single part" shall be understood to mean that the first container and the dispensing plunger are firmly connected to each other or that the first container and the dispensing plunger consist of just a single part. In an embodiment, the dispensing plunger is firmly connected to the first housing, for example by means of a screw, a nail, a clamp, a wedge or a rivet. In a further embodiment, the first container is designed appropriately such that a base surface of the first container forms the dispensing plunger. If the first container and the dispensing plunger are designed to be one-part, an input of force acting on the first container can be utilised directly to convey the monomer liquid from the second internal space into the first internal space. It is an advantage in this context that no additional components are required in order to effect an axial motion of the dispensing plunger, which renders the device easier and more reliable to use. It is another advantage that the input of force for shifting the dispensing plunger is applied axially onto the device, which reduces the force expended by the user.

Another embodiment of the device is characterized in that the first container contains a vessel with the monomer liquid. According to one embodiment, a vessel containing the monomer liquid shall be understood to mean all storage options, which can store the monomer liquid in hermetically sealed and sterile manner and which can be destroyed by an input of manual force. Examples of vessels containing the monomer liquid include glass ampoules, plastic ampoules, and plastic pouches. Glass ampoules are preferred because they are easy to sterilise and easy to open through the input of manual force.

Another embodiment of the device is characterized in that the first container includes an opening device for the vessel. According to one embodiment, an opening device shall be understood to be a device that is suitable for destroying the structural integrity of the vessel and for opening it in the process. According to one embodiment, the embodiment of the opening device shall be selected as a function of the structural stability of the vessel. According to one embodiment, the material of the opening device is suitable for destruction of the structural integrity of the material of the vessel. It is advantageous for the opening device to have a small diameter as compared to the surface of the vessel to be opened. This reduces the force expenditure required for opening the vessel. For example, the vessel can be opened by puncturing or cutting into it. Examples of opening devices comprise puncturing mandrels, needles, cannulas, and cutting edges. In a preferred embodiment, the vessel is a glass ampoule and the opening device is a puncturing mandrel. The puncturing mandrel is advantageous in that it can open the glass ampoule in a spot, while leaving the rest of the ampoule intact. In a further preferred embodiment, the vessel is a glass ampoule and the opening device is a puncturing mandrel arranged appropriately such that the puncturing mandrel opens an ampoule base of the glass ampoule. A typical glass ampoule includes an ampoule body, an ampoule head, and an ampoule base. The ampoule head is characterized by having a small diameter as compared to the ampoule body, which serves as a predetermined breakage site. It is customary to open the glass ampoule at the predetermined breakage site. Typically, the ampoule base has the same diameter as the ampoule body. It is advantageous according to one embodiment to break open the glass ampoule at the ampoule base. Firstly, using a puncturing mandrel to puncture the ampoule base, the glass ampoule is opened in a more controlled fashion due to the large difference in surface area between the opening device and the ampoule base. Secondly, the ampoule head being opened does not break off the remaining ampoule body, which reduces both the expenditure of force for opening and the number of fragments.

Another embodiment of the device is characterized in that the first container includes an axially shiftable conveying plunger, designed appropriately such that the vessel can be conveyed onto the opening device by the conveying plunger. According to one embodiment, a conveying plunger shall be understood to be an axially mobile component that can press the vessel onto the opening device and thus open it through a targeted axial shift within the first container.

According to one embodiment, the vessel is situated between the opening device and the conveying plunger. The conveying plunger can take a variety of shapes on the side facing the vessel. For example, the conveying plunger can be flat or can be shaped as a shoulder element. If the vessel is an ampoule, in one embodiment a glass ampoule, the conveying plunger is preferred to be shaped as a shoulder element. As described above, it is advantageous to open the glass ampoule at the ampoule base. Accordingly, the ampoule head points in the direction of the conveying plunger. A shoulder element is preferred, since the shoulder element attaches on the ampoule base rather than the ampoule head. The shoulder element is designed appropriately in this context such that contact takes place only with a shoulder, but not with the ampoule head of the vessel. In this context, the shoulder element is designed to be tubular, whereby the diameter of the hollow space is appropriate such that the ampoule head, but not the shoulder of the vessel, can be taken up into the shoulder element. Accordingly, the shoulder element protects the ampoule head from breaking off inadvertently. As a result, the force applied by the conveying plunger does not act on the predetermined breakage site and the ampoule head remains on the ampoule body, resulting in the advantages described above. According to one embodiment, the conveying plunger can be provided with a screw-type means at the end facing away from the vessel. The screw-type means is capable of effecting the axial shift of the conveying plunger by means of a thread. In one embodiment, the screw-type means can be designed in the form of a handle such that the input of force can be made more easily by the user. In an embodiment, the screw-type means can comprise an internal thread and the first container can comprise an external thread, whereby the threads engage in form-fitting and/or force-locking manner in order to shift the vessel onto the opening device by means of the conveying plunger.

Another embodiment of the device is characterized in that the first container can be axially inserted into the second container, at least in part. According to one embodiment, the term "can be inserted" shall be understood to mean that a cross-sectional circumference of the first container can be fully taken up into the second container. Inserting the first container into the second container reduces a total length of the device by the length of the first container that is being shifted into the second container. After the vessel is opened and the monomer liquid flows from the vessel into the second internal space, a first shift of the first container into the second container can convey the monomer liquid from the second internal space into the first internal space. After the first shift, the bone cement made of bone cement powder and monomer liquid is produced in the first internal space. In a preferred embodiment, subsequently, the bone cement thus produced can be dispensed from the device through a second shift of the first container into the second container. This is advantageous in that both the production and the dispensation of the bone cement are implemented sequentially through a similar working step, in particular in the absence of additional external apparatuses or conversion measures. Accordingly, the user cannot confuse working steps. As another advantage of inserting the first container into the second container, the vessel does not need to be destroyed completely. After the vessel is opened in a spot, no further force needs to be applied to the vessel, the vessel can be kept intact except for the opened spot. This reduces not only the force expended by the user of the device, but also the production of fragments of the vessel with the disadvantages described above.

Another embodiment of the device is characterized in that the first container includes an external thread and the second container includes an internal thread, whereby the external thread and the internal thread are connected or can be connected to each other in form-fitting and/or force-locking manner. External thread and internal thread appropriately acts in concert such that the first container can be shifted into the second container by means of a relative rotary motion of the two containers with respect to each other. In general, the shift of the first container into the second container can take place in different ways. For example, the first container can be pushed by pressure onto an end facing away from the second container. One advantage of the shift by means of external and internal thread is that the force expended by the user can be reduced. In one embodiment, the external and/or internal thread are designed to be self-locking such that the relative rotation of the two containers with respect to each other can be performed only in the direction of the first container being shifted into the second container. Firstly, the self-locking can reduce the requisite force to be expended by the user even further, since no force acting against a reverse rotation of the first container from the second container needs to be expended. Secondly, the self-locking increases the risk of a user error, since a use of the device, once started, can always take place in predetermined direction only. Accordingly, for example an inclusion of air bubbles into the bone cement can be prevented.

Another embodiment of the device is characterized in that the device includes a fluid-conducting conveying means. According to one embodiment, a fluid-conducting conveying means shall be understood to be a structure that separates internal spaces of a container in appropriate manner such that a gas and liquid exchange between the internal spaces can take place, whereas an exchange of solids is essentially prevented. Examples of fluid-conducting conveying means include pore disks, screens, nets, and membranes.

A second subject matter of the present embodiment relates to a method for the provision of a bone cement from two starting components by means of a device comprising a hollow cylinder-shaped first container, in which a monomer liquid as a first starting component is stored, a hollow cylinder-shaped second container comprising a container wall, a first internal space, and a second internal space, whereby a bone cement powder as second starting component is stored in the first internal space, and whereby the monomer liquid can be conveyed into the second internal space, a fluid-conducting conveying means arranged between the first internal space and the second internal space, whereby the first container and the second container are axially connected to each other, comprising at least the following sub-steps in sequence:
  a. opening the vessel;
  b. the monomer liquid flowing about the dispensing plunger into the second internal space;
  c. conveying the monomer liquid from the second internal space into the first internal space through a first shift of the first container into the second container;
  d. production of the bone cement from bone cement powder and monomer liquid.

Another embodiment of the method is characterized in that the bone cement is dispensed from the device in a sub-step e) through a second shift of the first container into the second container. In general, the bone cement can be dispensed from the device in a variety of ways. The dispensation can take place, for example, by means of levers attached to the second container or by a separate, separately-connected dispensing pump. The dispensation is preferred to take place without separate external apparatuses and without additional components on the device. Due to the second shift of the first container into the second container, no separately-required dispensing pumps and no separate components, such as levers, are required. It is therefore an advantage that the use of the device is being simplified and that the risk of an error occurring during the use of the device is reduced.

The device according to one embodiment is characterized in that it provides bone cements made of two starting components. According to one embodiment, a bone cement shall be understood to be a substance that is well-suited to provide a stable connection between artificial joints, such as, for example, hip and knee joints, and bone material in the realm of medical technology. In one embodiment, bone cements are polymethylmethacrylate bone cements (PMMA bone cements). PMMA bone cements have been used in medical applications for a long period of time and are based on the pioneering work of J. Charnley (cf. Charnley, J. Anchorage of the femoral head prosthesis of the shaft of the femur. J. Bone Joint Surg. 1960; 42, 28-30). In this context, PMMA bone cements can be produced from a bone cement powder as first starting component and a monomer liquid as second starting component. If the composition is appropriate, the two starting components separated from each other can be stable on storage. When the two starting components are contacted to each other, the polymer components of the bone cement powder are generated by swelling forming a plastically deformable bone cement, which is also referred to as bone cement dough. A polymerisation of the monomer by radicals is initiated in this context. Upon advancing polymerisation of the monomer, the viscosity of the bone cement dough increases until the bone cement dough solidifies completely.

According to one embodiment, a bone cement dough shall be understood to be a powder, which includes at least one particulate polymethylmethacrylate and/or one particulate polymethylmethacrylate copolymer. Examples of copolymers include styrene and/or methylacrylate. In an embodiment, the bone cement powder can comprise, in addition, a hydrophilic additive that supports the distribution of the monomer liquid within the bone cement powder. In a further embodiment, the bone cement powder can comprise, in addition, an initiator that initiates the polymerisation. In a further embodiment, the bone cement powder can comprise, in addition, a radiopaquer. In yet a further embodiment, the bone cement powder can comprise, in addition, pharmaceutically active substances, such as, for example, antibiotics.

In one embodiment, the bone cement powder includes at least one particulate polymethylmethacrylate and/or one particulate polymethylmethacrylate copolymer, an initiator, and a radiopaquer or it consists of the components. Also preferably in one embodiment, the bone cement powder includes at least one particulate polymethylmethacrylate and/or one particulate polymethylmethacrylate copolymer, an initiator, a radiopaquer, and a hydrophilic additive or it consists of the components. In one embodiment, the bone cement powder includes at least one particulate polymethylmethacrylate and/or one particulate polymethylmethacrylate copolymer, an initiator, a radiopaquer, a hydrophilic additive, and an antibiotic or it consists of the components.

According to one embodiment, the particle size of the particulate polymethylmethacrylate and/or of the particulate polymethylmethacrylate copolymer of the bone cement powder can correspond to the sieved fraction of less than 150 μm, in one embodiment of less than 100 μm.

According to one embodiment, the hydrophilic additive can be particulate and/or fibrous in shape. In a further embodiment, the hydrophilic additive is poorly soluble, in one embodiment insoluble, in methylmethacrylate. In a further embodiment, the hydrophilic additive can possess an absorption capacity of at least 0.6 g methyl methacrylate per gram of hydrophilic additive. In a further embodiment, the hydrophilic additive can comprise a chemical substance with at least one OH group. In this context, one embodiment can preferably provide the hydrophilic additive to possess covalently bound OH groups on its surface. Examples of the preferred hydrophilic additives can be additives selected from the group comprising cellulose, oxycellulose, starch, titanium dioxide, and silicon dioxide, whereby pyrogenic silicon dioxide is particularly preferred. In an embodiment, the particle size of the hydrophilic additive can correspond to the sieved fraction of less than 100 µm, in one embodiment of less than 50 µm, and most in one embodiment of less than 10 µm. The hydrophilic additive can be present in an amount of up to 0.1 to 2.5 wt. %, relative to the total weight of the bone cement powder.

According to one embodiment, the initiator can contain dibenzoyl peroxide or consist of dibenzoyl peroxide.

According to one embodiment, a radiopaquer shall be understood to be a substance that allows the bone cement to be visualised on diagnostic radiographs. Examples of radiopaquers can include barium sulfate, zirconium dioxide, and calcium carbonate.

According to one embodiment, the pharmaceutically active substance can comprise one or more antibiotics and, if applicable, added cofactors for the one or more antibiotics. In one embodiment, the pharmaceutically active substance consists of one or more antibiotics and, if applicable, added cofactors for the one or more antibiotics. Examples of antibiotics include, inter alia, gentamicin, clindamycin, and vancomycin.

According to one embodiment, the monomer liquid can comprise the methylmethacrylate monomer or consist of methylmethacrylate. In an embodiment, the monomer liquid includes, aside from the monomer, an activator that is dissolved therein, such as, for example, N,N-dimethyl-p-toluidine, or consist of methylmethacrylate and N,N-dimethyl-p-toluidine.

EXAMPLES

Embodiments are illustrated further by examples in exemplary manner in the following. The embodiments shall not be limited to the examples.

FIG. 1 illustrates a device 100 in a starting state. The device 100 is single-part, but made up of multiple components. The device 100 includes a first container 200 and a second container 300. The device 100 is tube-like in shape. The first container 200 and the second container 300 are axially connected to each other. The first container 200 and the second container 300 are jointly arranged on the centre axis of the device 100. The first container 200 projects into the second container 300. The first container 200 seals the second container 300 with respect to the surroundings of the device 100.

The first container 200 possesses an external thread 240 on a part of its external surface 201. A screw-type means 231 is arranged on a first end 202 of the first container 200. The screw-type means 231 surrounds the first end 202 of the first container 200 in a bonnet-like manner. The screw-type means 231 has an internal thread 232 that acts in concert with the external thread 240 in a form-fitting and/or force-locking manner. The screw-type means 231 is shaped in the form of a handle. The shape of a handle allows the input of force for the opposite rotation of the first container 200 with respect to the second container 300 to be applied more easily by the user. The internal thread 232 is not fully rotated onto the external thread 240 such that a hollow space A 235 exists between screw-type means 231 and first container 200. A conveying plunger 230 in the form of a shoulder element is arranged on the screw-type means 231. The conveying plunger is shaped to have a cross-section shaped like an H. The conveying plunger 230 projects from the first end 202 into the first container 200. The conveying plunger 230 in the form of a shoulder element is designed appropriately such that a contact can come to exist only with a shoulder 212, but not with a head 213 of a vessel 210. In this context, the conveying plunger 230 is designed to be tubular, whereby the diameter of the hollow space is appropriate such that the head 213 of the vessel 210, but not the shoulder 212 of the vessel 210, can be taken up. Accordingly, the conveying plunger 230 protects the head 213 of the vessel 210 from breaking off in an uncontrolled manner. The conveying plunger 230 can therefore act only on the shoulder 212 of the vessel 210. The first container 200 possesses a second end 203 with an opening device 220 in the form of a puncturing mandrel.

A monomer liquid 211 is stored in the first container 200. The monomer liquid 211 is stored in the vessel 210 in the form of a glass ampoule in this context. The vessel 210 is in one embodiment provided as a glass ampoule since the monomer liquid 211 can be stored hermetically sealed and sterile in a glass ampoule. The vessel 210 is further preferred to be provided as a glass ampoule, since a glass ampoule is easy to open. The vessel 210 is stored in appropriate manner between the opening device 220 and the conveying plunger 230 such that the vessel 210 cannot move freely in the first container 200. By this means, an uncontrolled motion of the vessel 210 and thus an inadvertent breakage or opening of the vessel is prevented. The vessel 210, the opening device 220, and the first container 200 form a hollow space B 236.

A dispensing plunger 400 is attached to an external side of the second end 203 of the first container 200. The dispensing plunger 400 is cambered on a top side 401 facing the first container. The dispensing plunger 400 is firmly connected to the first container 200. The dispensing plunger 400 is connected to the first container 200 in a form-fitting and/or force-locking manner. The dispensing plunger is connected to the second end 203 of the first container 200 by means of a screw-type device 410. The dispensing plunger 400 and the first container 200 are designed to be one-part. An external surface 420 of the dispensing plunger 400 borders on a container wall 310 of the second container 300. The dispensing plunger includes two sealing rings 430 on the external surface 420.

The second container possesses an internal thread 302 on a first end 301. A threaded sleeve 303 with an internal thread 350 is applied to the internal thread 302. The internal thread 350 can act in concert with the external thread 240 in a form-fitting and/or force-locking manner. The threaded sleeve 303 and the internal thread 302 and the external thread 350 form a coaxial double pair of threads. The use of a threaded sleeve 303 allows the first container 200 to be designed with a smaller diameter than if no threaded sleeve 303 was used. This reduces the risk of the first container 200 and second container 300 becoming wedged during the use of the device 100. The threaded sleeve 303 prevents the first container 200 from being pulled fully out of the second container 300, since the threaded sleeve forms an undercut for the second end 203 of the first container 200. The second end 203 of the first container 200 includes an external diameter and the threaded sleeve 303 includes an internal diameter, whereby the external diameter of the first end 203 is larger than the internal diameter of the threaded sleeve 303. This reduces the risk of inadvertent opening and therefore contaminating the device 100. The second container 300 possesses a first internal space 320 and a second internal space 330. A bone cement powder 321 is stored in the first internal space 320. The entire second internal space 330 is filled with the bone cement powder 321. The bone cement powder 321 is appropriately compacted in the first internal space 320 such that the bone cement powder 321 is not freely mobile. A gas is situated in the intervening spaces of the bone cement powder 321. The first internal space 320 is connected to the second internal space 330 by means of a fluid-conducting conveying means 340. The conveying means 340 is designed to be permeable to gases and liquids, but impermeable to solids, such as, for example, the bone cement powder 321. The conveying means 340 includes two sealing rings 341 in the direction of the container wall 310.

The second internal space 330 borders, in a top section, on the dispensing plunger 400. The dispensing plunger 400 in a first position is situated at the level of a first subsection 311 of the second container 300. The first subsection 311 possesses at least one recess 312 in the container wall 310. The recess 312 extends in axial direction of the second container 300. The axial extension of the recess 312 is longer than that of the dispensing plunger 400. The recess 312 is designed appropriately such that the monomer liquid 211 can flow about the dispensing plunger 400 at the level of the first subsection 311 and can thus enter into the second internal space 330.

Figure 2:
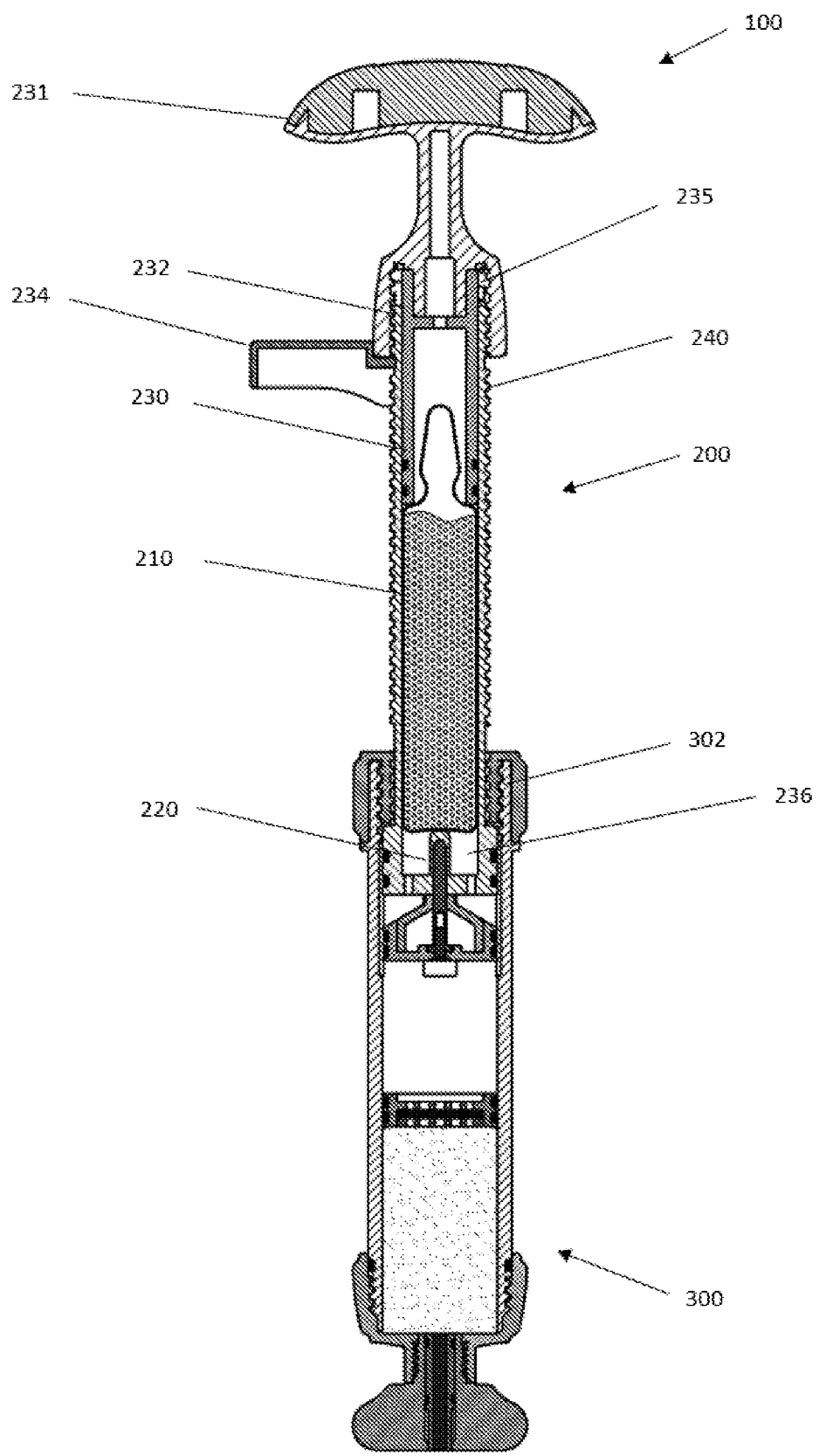
FIG. 2 illustrates the device from FIG. 1 rotated by 90° in clockwise direction

FIG. 2 illustrates the device 100 from FIG. 1 rotated by 90° in clockwise direction. The screw-type means 231 is shaped as a handle for a hand. To prevent the conveying plunger 230 from being screwed in inadvertently, a locking element 234 is attached on the external thread 240 right below the screw-type means 231. The locking element 234 blocks the external thread 240 for the screw-type means 231. With the locking element 234 applied, it is not possible to fully rotate the internal thread 232 of the screw-type means 231 onto the external thread 240. With the locking element 234 applied, the hollow space A 235 is maintained between screw-type means 231 and first container 200. Accordingly, the conveying plunger 230 can not press the vessel 210 onto the opening device 220. With the locking element 234 applied, a hollow space B 236 is maintained between opening device 220, vessel 210, and first container 200. The locking element 234 can be pulled off perpendicular to the longitudinal axis of the device 100. The axial extension of the hollow space A 235 is appropriate such that rotating the screw-type means 231 down onto the external thread 240, and thus conveying the vessel 210 onto the opening device 220, destroys the structural integrity of the vessel 210 in a spot. The axial extension of the hollow space A 235 is short enough such that the vessel 210 is punctured only in a spot without being destroyed completely. An axial extension of the hollow space B 236 is in one embodiment advantageously at least equal in length to an axial extension of the hollow space A 235 since, as a result, the vessel 210 can be opened only in a spot by rotating the screw-type means 231 downward.

Figure 3:
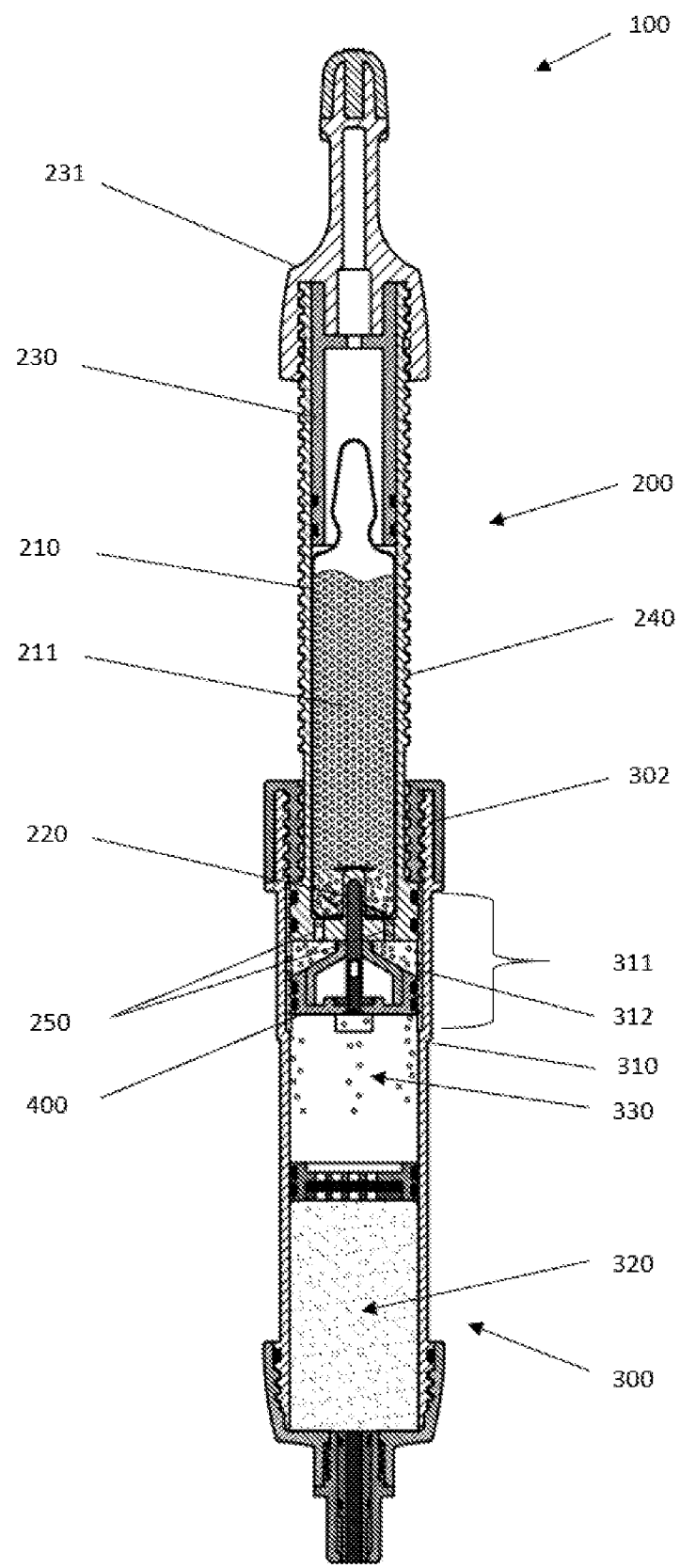
FIG. 3 illustrates the device from FIG. 2 while a vessel with monomer liquid is being opened

FIG. 3 illustrates, by comparison to FIG. 2, the device 100 after removal of the locking element 234 (see FIG. 2) and with the conveying plunger 230 rotated downward. The screw-type means 231 has been rotated fully onto the external thread 240. The screw-type means 231 was rotated onto the external thread 240 in appropriate manner such that no hollow space A 235 (see FIG. 2) exists any longer between screw-type means 231 and external thread 240. In a first motion, the conveying plunger 230 pushed the vessel 210 onto the opening device 220 and thus opened it. The conveying plunger has pressed the vessel 210 onto the opening device 220 in appropriate manner such that no hollow space B 236 (see FIG. 2) exists any longer between the first container 200, opening device 220, and vessel 210. The opening device destroyed the structural integrity of the vessel 210 in a spot. After the screw-type means 231 is rotated down onto the external thread 240, and thus after the vessel 210 is opened, continued opposite rotation of the first container 200 with respect to the second container 300 has no effect on the device 100. This serves to reduce safety risks related to the incorrect use of the device 100. The exclusive purpose of screwing the screw-type means 231 down onto the external thread 240 is to open the vessel 210. Further process steps need to be initiated separately. This prevents a user from not allowing the monomer liquid 211 enough time after the vessel 210 is opened to flow from the vessel 210 into the second internal space 330. The second internal space 330 is spatially arranged above the first internal space 320. The vessel 210 being opened allows the monomer liquid 211 to flow from the vessel 210 under the action of gravity. The monomer liquid 211 flows under the action of gravity through at least one feedthrough 250 in the base of the first container 200 in the direction of the dispensing plunger 400. The dispensing plunger in the first position is situated at the level of the first subsection 311. The monomer liquid 211 flows about the dispensing plunger 400 through the recesses 312 in the container wall 310 into the second internal space 330. The monomer liquid 211 flows about the dispensing plunger 400 by means of the recesses 312 in the first subsection 311. The second internal space 330 includes a volume that corresponds at least to the volume of the monomer liquid 211. The second internal space 330 can take up all of the monomer liquid 211.

Figure 4:
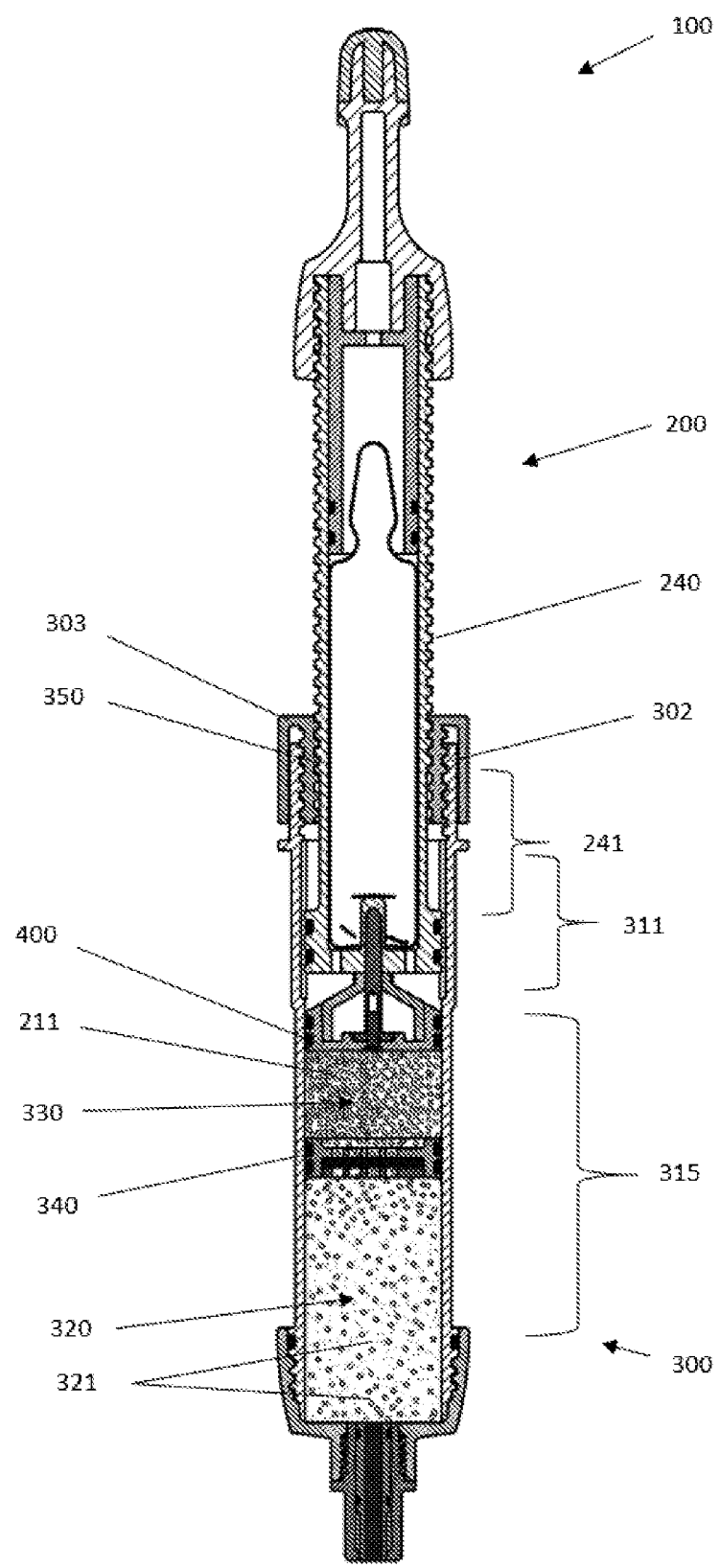
FIG. 4 illustrates the device from FIG. 3 while the monomer liquid is being conveyed into a first internal space

FIG. 4 illustrates, by comparison to FIG. 3, the first container 200 being inserted into the second container 300 by means of a first axial shift. In the course of the first axial shift, the first container 200 was pushed down, in a first step, into the second container 300 over a distance that corresponds to a length of a section 241 of the first container 200 that has no external thread. The length of the section 241 is such that the dispensing plunger 400 is shifted from the level of the first subsection 311 to the level of a second subsection 315. The second subsection 315 includes no recesses in the container wall 310. The dispensing plunger 400 separates, at the level of the second subsection 315, the second internal space 330 in fluid-impermeable manner in the direction of the first container 200. The first step serves to separate the monomer liquid 211 in the internal space 330 with respect to the first container 200 in sealed manner. The first step of the first axial shift therefore serves to reduce the safety risks related to the incorrect use of the device 100. The first step of the first axial shift makes sure that all of the monomer liquid 211 that has flown into the second internal space 330 is available for further process steps and cannot flow back into the first container 200.

After completion of the first step, the device 100 is rotated appropriately such that the first internal space 320 is spatially arranged above the second internal space 330. This is advantageous in that any subsequent conveying of the monomer liquid 211 into the first internal space 320 proceeds spatially from bottom to top. Accordingly, a gas that is present between the individual particles of the bone cement powder 321 can escape in upward direction upon the monomer liquid 211 being conveyed into the first internal space 320, which reduces the risk of air inclusions being present in the bone cement.

In a second step of the first axial shift, the external thread 240 of the first container 200 acts in concert with the internal thread 302 of the second container 300 in form-fitting and/or force-locking manner by means of a rotation about the longitudinal axis of the device 100. In this context, the action can take place through a direct contact of the internal thread 302 with the external thread 240 or by an action of the threaded sleeve 303. The figure illustrates the acting in concert by means of the threaded sleeve 303. In the following, the first axial shift is continued via an opposite rotation of the first container 200 relative to the second container 300. The device 100 is designed appropriately such that the opposite rotation of the first container relative to the second container 300 can take place in the direction of the first axial shift only. The device 100 is designed appropriately such that, after the onset of the second step of the first axial shift, the first container 200 and the second container 300 can no longer be unscrewed from each other. This is advantageous, on the one hand, in that a user does not need to expend additional force in order to prevent the device 100 from rotating back. On the other hand, a risk of air bubbles forming is reduced.

Due to the first axial shift of the first container 200 into the second container 300, the dispensing plunger 400 has been shifted from the first subsection 311 into a second subsection 315 and the conveying of the monomer liquid 211 into the first internal space 320 has commenced. Continuing the first axial shift of the first container 200 into the second container 300 presses the monomer liquid from the second internal space 330 via the conveying means 340 into the bone cement powder 321 in the first internal space 320.

Figure 5:
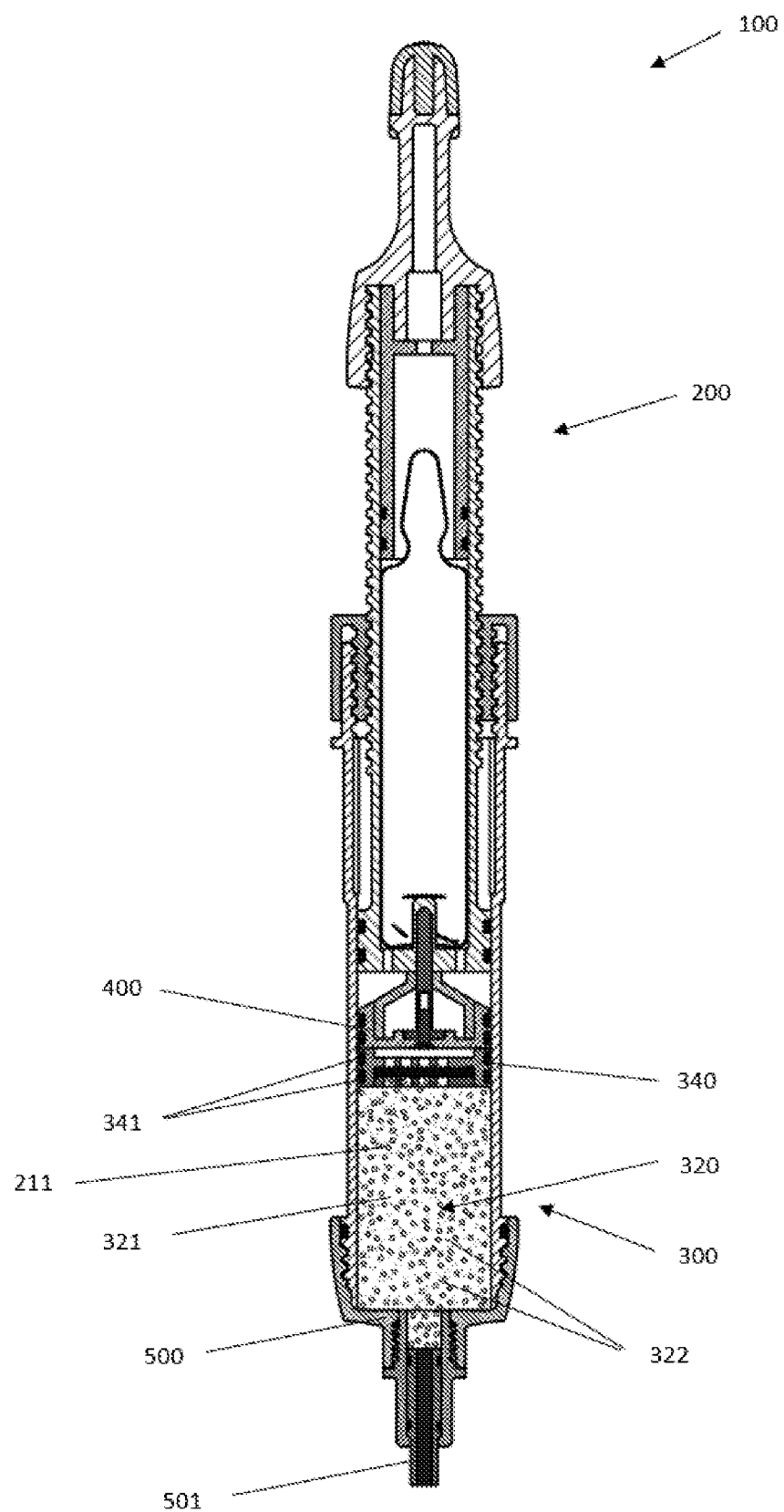
FIG. 5 illustrates the device from FIG. 4 while the bone cement is being formed

FIG. 5 illustrates the device 100 after completion of the first axial shift. The first axial shift is completed when the dispensing plunger 400 reaches the conveying means 340. The conveying means 340 having been reached is indicated to a user of the device 100 by an increased counter-pressure during the opposite rotation of the container 200 with respect to the second container 300. On the one hand, the conveying means 340 is firmly locked in the second container 300 in appropriate manner such that the bone cement powder 331 can be stored in the first internal space 320 in compacted form and such that a user experiences a noticeable counter-pressure upon completion of the first axial shift. On the other hand, the conveying means 340 is easy enough to shift in the second container 300 such that a user has no difficulty shifting the conveying means 340 during the further use of the device 100. The conveying means 340 includes two sealing rings 341 on an external surface. The sealing rings 341 provide a compromise between firm locking and easy shifting ability of the conveying means 340. All of the monomer liquid 211 has been conveyed into the first internal space 320. The monomer liquid 211 displaced the gas in the intervening spaces of the bone cement powder 321. The gas in the intervening spaces of the bone cement powder 321 is forced in the direction of a dispensing opening 500, which is arranged to be adjacent to the first internal space 320. The dispensing opening 500 is provided with a closing pin 501. The closing pin 501 prevents the bone cement powder 321 from being dispensed inadvertently from the device 100. The closing pin 501 is designed to be permeable to gases, and optionally also to the monomer liquid 211. The gas from the intervening spaces of the bone cement powder 321 has been expelled from the device 100 through the closure pin 501.

After completion of the first axial shift, all of the bone cement powder 321 is wetted by the monomer liquid 211. Once the bone cement powder 321 is completely wetted by the monomer liquid 211, the volume of the bone cement powder 321 expands. During the expansion of the bone cement powder 321, the closing pin 501 is expelled partially out of the dispensing opening 500. This indicates to the user that the device 100 works properly and that the bone cement powder 321 is wetted completely by the monomer liquid 211. The mixing of bone cement powder 321 and monomer liquid 211 leads to the formation of a bone cement 322. Combining bone cement powder 321 and monomer liquid 211 results in swelling of the bone cement powder 321.

Figure 6:
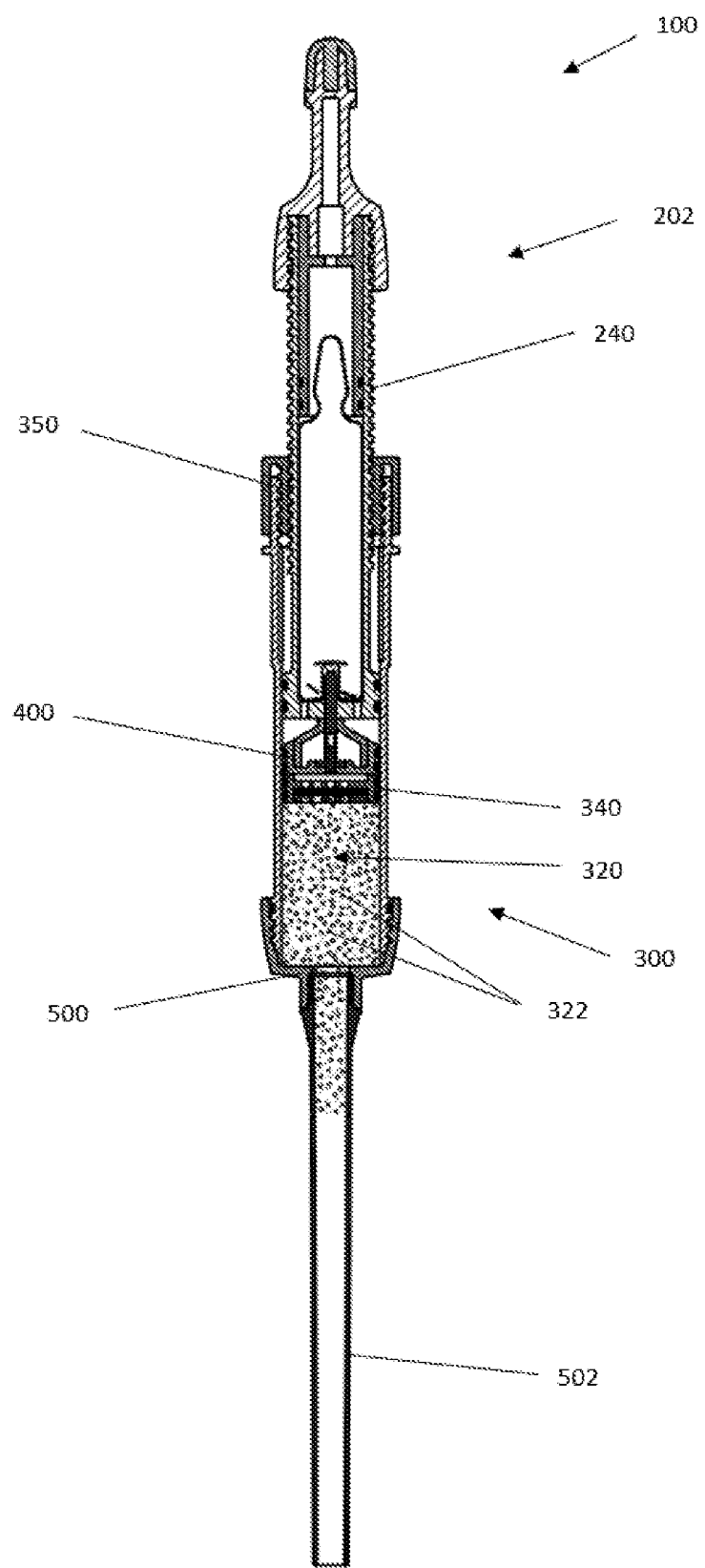
FIG. 6 illustrates the device from FIG. 5 while the bone cement is being dispensed

FIG. 6 illustrates the device 100 during a second axial shift of the first container 200 into the second container 300. The closing pin 501 (see FIG. 5) has been replaced by a dispensing cannula 502. The second axial shift is effected through a continued opposite rotation of the first container 200 with respect to the second container 300 about the longitudinal axis of the device 100, whereby the internal thread 350 of the threaded sleeve 303 acts in concert with the external thread 240 in a form-fitting and/or force-locking manner. During the second axial shift, the dispensing plunger 400 pushes the conveying means 340 in the direction of the dispensing opening 500. The second axial shift of the first container 200 into the second container 300 conveys the bone cement 322 from the internal space 320 out of the device 100 into the dispensing cannula 502.

Figure 7:
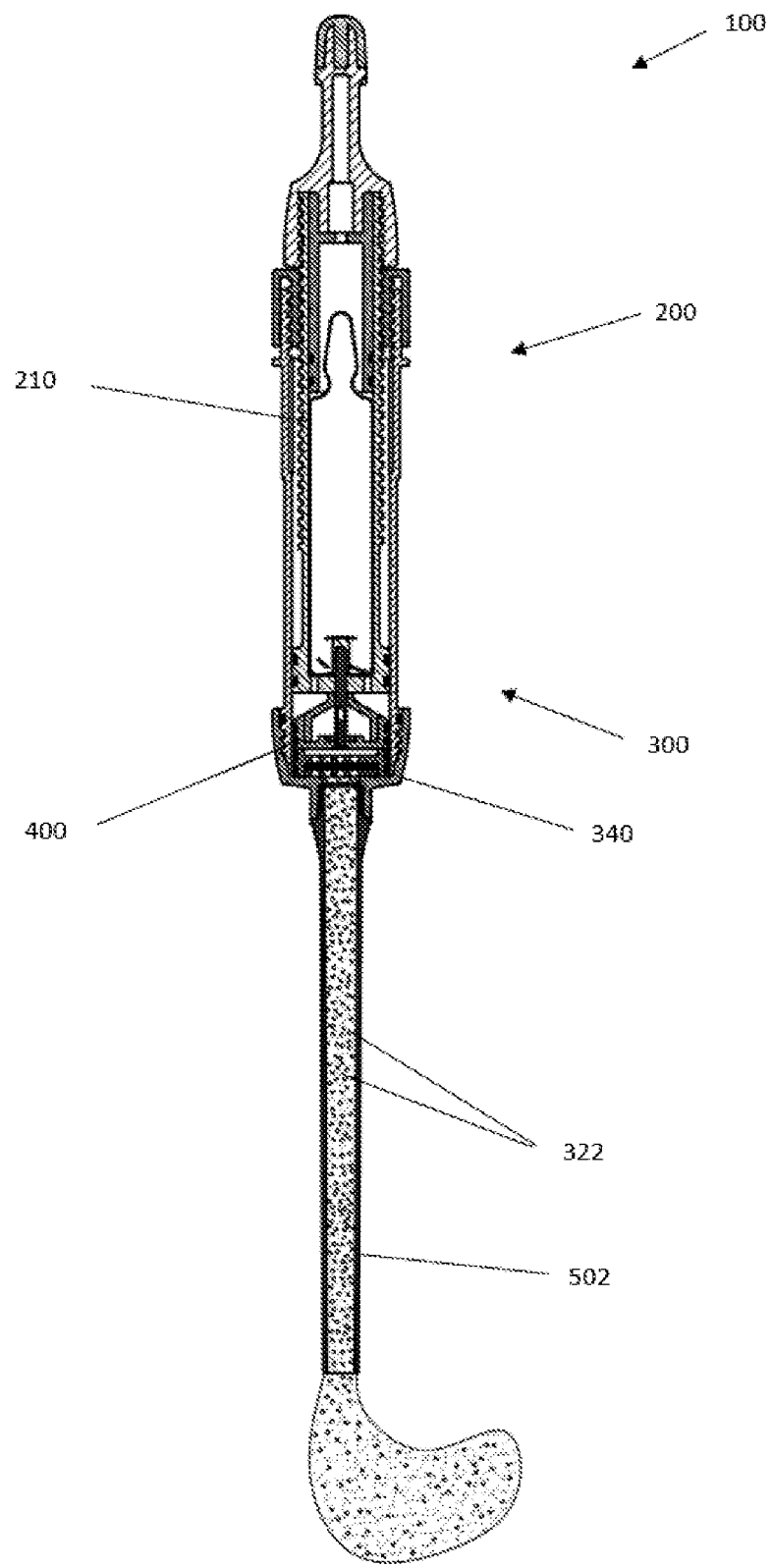
FIG. 7 illustrates the device from FIG. 6 after completion of the dispensation process

FIG. 7 illustrates the device 100 after completion of the second axial shift of the first container 200 into the second container 300. The conveying means 340 has been pushed all the way to the base of the second container 300 by the dispensing plunger 400. The bone cement 322 has been extruded completely from the device 100. The dispensing cannula 502 affords the application of the bone cement 322 at the desired site. The dispensing cannula 502 is still filled with residual bone cement 322. Due to the first container 200 being inserted into the second container 300, the device 100 adopted a shorter axial extension. The vessel 210 is not completely destroyed after completion of the dispensation of the bone cement 322. The vessel 210 is only opened in a spot by the opening device 220 after completion of the dispensation of the bone cement 322.

FIG. 1 to FIG. 7 illustrate the device 100 during the provision and mixing of the starting components and the dispensation of the bone cement 322. A user starts by removing the locking element 234 from the external thread 240 of the first container 200. The purpose of the locking element 234 is to prevent the vessel 210 with the monomer liquid 211 from being opened inadvertently. Once the locking element 234 is removed, the user screws down the screw-type means 231, which is initially not fully rotated onto the external thread 240 of the first container 200. The screw-type means 231 acts on the conveying plunger 230 in this context such that the latter is being pushed further into the first container 200. In this regard, the conveying plunger 230 must be arranged in the first container 200 such as to be axially mobile. The screw action of the screw-type means 231 results in an axial motion of the conveying plunger 230 towards the vessel 210. In the process, the conveying plunger 230 transfers—essentially—the axial motion of the screw-type means 231 to the shoulder of the vessel 210 in order to press the latter onto the opening device 220 and to thus open it in a spot. The conveying plunger 230 serves as a transfer means of the force on the vessel 210, which is generated in the thread when the screw-type means 231 is being screwed onto the external thread 240 and is directed into the device 100. The shoulder 212 of the vessel 210 is structurally sufficiently sound such that the vessel 210 is opened adjacent to the opening device 220 only. In one variant, the screw-type means 231 can be screwed down onto the external thread 240 only to the extent such that the vessel 210 is destroyed in a spot, but not completely.

Once the screw-type means 231 is rotated completely onto the external thread 240, continuing the rotary motion leads to no further axial motion of the conveying plunger 230. Only the first container 200 can then be rotated by its longitudinal axis within the device 100. If the vessel 210 is opened, the monomer liquid 211 flows from the inside of the vessel 210 in the direction of the dispensing plunger 400. As described above, the dispensing plunger 400 in the first position is permeable to the monomer liquid 211. In order to convey the monomer liquid 211 into the second internal space 330, the device 100 is held appropriately such that the container 200 is spatially situated above the second container 300. By this means, gravity is utilised to convey the monomer liquid 211 into the second internal space 330, which is the reason why no external apparatus, such as, for example, a pump or a vacuum connection, is required. In order to provide for essentially complete transfer of the monomer liquid 211 into the second internal space 330, the device 100 can be held in the orientation described above, with the second container 300 downwards, for a period of time of 60 seconds, in particular 30 seconds, in one embodiment, 10 seconds. To prevent the monomer liquid 211 from flowing back into the first container 200 after it is conveyed into the second internal space 330, the first container 200 is pushed, at least in part, into the second container 300 by means of the first axial motion. This transfers the conveying plunger 400 from the first position into the second position. Accordingly, the monomer liquid 211 can no longer flow back through the recess 312 in the direction of the first container 200.

Subsequently, the device 100 is rotated appropriately such that the second container 300 is spatially arranged above the first container 200. This is advantageous in that the gas that is present in the second internal space 330 and between the particles of the cement powder 321 is displaced in the direction of the dispensing opening 500, when the monomer liquid 211 is subsequently conveyed from the second internal space 330 into the first internal space 320.

Conducting the gas specifically in the direction of the dispensing opening 500 of the device 100 reduces the risk of gas inclusions being present within the mixed bone cement 322.

To convey the monomer liquid 211 from the second internal space 330 into the first internal space 320, a force acting on the dispensing plunger 400 in the direction of the conveying means 340 is required. For this purpose, the external thread 240 of the first container 200 acts in concert with the internal thread 302 of the second container 300. The acting in concert can take place directly—i.e. form-fitting and/or force-locking—or, as illustrated, through the aid of a threaded sleeve 303. For this purpose, the user rotates the screw-type means 231 appropriately such that the external thread 240 engages the internal thread 350 of the threaded sleeve 303 and such that the first container 200 is screwed into the second container 300 by means of the rotary motion. In one embodiment, the screw-in process can be made to be non-reversible, which also reduces a generation of gas inclusions. A corresponding non-return lock ensures that in the case of the conveying being interrupted, forces possibly built up in the device 100 do not increase a distance between dispensing plunger 400 and the conveying means 340, in particular dispensing opening 500.

The first axial shift is completed when the dispensing plunger 400 reaches, in particular touches on, the conveying means 340. At this point in time, the conveying of the monomer liquid 211 into the first internal space 320 is completed. The completion of the first axial shift is indicated to the user by means of an increased counter-pressure while rotating the screw-type means 231 and by the closing pin 502 being partially expelled.

Before the user initiates the second axial shift by continuing to rotate the screw-type means 231, the device remains in the above-described position in order to allow the bone cement 322 sufficient time to be produced. The period of time depends on the composition and properties of the starting materials and can be a period from 5 seconds to 5 minutes. Subsequently, the second axial shift of the first container 200 into the second container 300 is initiated. Depending on the application site of the bone cement 322, it makes sense to provide the device 100 with the dispensing cannula 502 on the dispensing opening 500 before dispensing the bone cement 322. The second axial shift is continued until the desired amount or all of the bone cement 322 has been dispensed from the device 100. The spatial orientation of the device 100 during the second axial shift can be selected arbitrarily, according to need.

Figure 8:
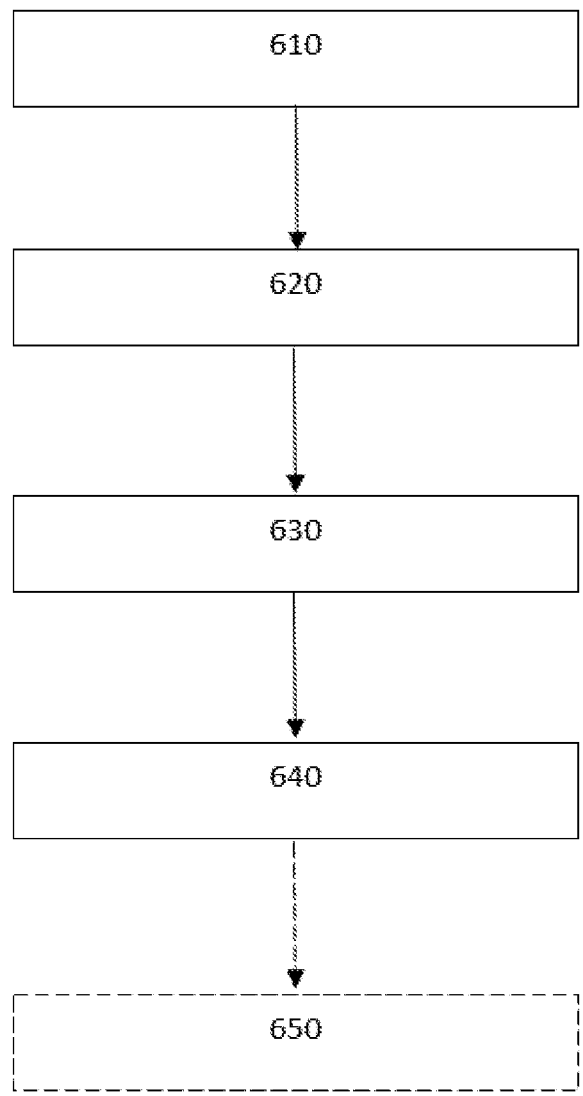
FIG. 8 illustrates a flow diagram (Method for the provision of a bone cement from two starting components)

FIG. 8 illustrates a flow diagram containing steps 610 to 650 of a method 600 for the provision of a bone cement from two starting components by means of the device 100 comprising the hollow cylinder-shaped first container 200, in which the monomer liquid 211 as first starting component is stored in the vessel 210, the hollow cylinder-shaped second container 300 comprising the container wall 310, the first internal space 320, and the second internal space 330, whereby the bone cement powder 321 as second starting component is stored in the first internal space 320, and whereby the monomer liquid 211 can be conveyed into the second internal space 330, the fluid-conducting conveying means 340 arranged between the first internal space 320 and the second internal space 330, whereby the first container 200 and the second container 300 are axially connected to each other. In a preferred embodiment of the method 600, the vessel 210 is a glass ampoule since a glass ampoule is easy to sterilise and to destroy. In a further preferred embodiment of the method 600, the dispensing plunger 400 is situated at the level of a first position within the second vessel 300. The first position is characterized in that the container wall 310 bordering on the dispensing plunger 400 includes recesses 312.

The vessel 210 is opened in a first step 610. In one embodiment, the vessel 210 is opened in a spot only and is not destroyed completely. In a preferred embodiment of the method 600, the first container 200 is spatially arranged above the second container 300 before the step 610 such that the monomer liquid 211 can flow downwards in the direction of the second container 300 through the force of gravity. In a further preferred embodiment of the method 600, step 610 takes place through rotating downwards the conveying plunger 230, which presses the vessel 210 onto the opening device 220 in the form of a puncturing mandrel and thus opens it in a spot.

In a second step 620, the monomer liquid 211 flows out of the vessel 210, about the dispensing plunger 400 into the second internal space 330. In a further preferred embodiment of the step 620, the monomer liquid 211 flows about the dispensing plunger 400 via at least one recess 312 in the container wall 310. In a further preferred embodiment of the step 620, the monomer liquid 211 flows about the dispensing plunger 400 via recesses 312 in the form of a groove. In a preferred embodiment of the step 620, the dispensing plunger 400 is cambered in order for all of the monomer liquid 211 to be conducted in the direction of the recesses 312.

In a third step 630, the monomer liquid 211 is conveyed out of the second internal space 330 into the first internal space 320 through a first shift of the first container 200 into the second container 300. In a preferred embodiment of the step 630, the dispensing plunger 400 is inserted from the first position into a second position in the course of a first step. The second position is characterized in that the container wall 310 bordering on the dispensing plunger 400 is designed to be free of recesses. The monomer liquid 211 cannot flow about the dispensing plunger 400 at the level of the second position. The dispensing plunger 400 seals the second internal space 330 at the level of the second position to liquids and solids with respect to the first container 200. In a further preferred embodiment of the step 630, the device 100 is rotated appropriately after the first step such that the second container 300 is spatially arranged above the first container 200. As a result, a gas present between the particles of the bone cement powder 321 can be displaced from the bone cement powder 321 by the monomer liquid 211 with less trouble, with a reduced risk of air inclusions in the further course of the method 600. In a further preferred embodiment of the step 630, the first container 200 includes an external thread 240 and the second container 300 includes an internal thread 302, whereby external thread 240 and internal thread 302 can act in concert in form-fitting and/or force-locking manner in order to shift the first container 200 into the second container 300. In a further preferred embodiment of the step 630, the device includes a threaded sleeve 303. The threaded sleeve and the internal thread 302 and the external thread 240 form a coaxial double pair of threads. In a second step of the first axial shift, the external thread 240 and the internal thread 302 act in concert appropriately, in one embodiment by means of the threaded sleeve 303, such that the first container 200 is inserted into the second container 300. The second step of the first axial shift conveys the monomer liquid 211 from the second internal space 330 into the first internal space 320.

In a fourth step 640, the production of the bone cement 322 from bone cement powder 321 and monomer liquid 211 takes place. In a preferred embodiment of the step 640, the production of the bone cement 322 starts with the bone cement powder 321 being wetted by the monomer liquid 211. Once wetted, the bone cement powder 321 swells.

In an optional fifth step 650, the bone cement 322 is dispensed from the device 100 through a second shift of the first container 200 into the second container 300. In a preferred embodiment of the step 650, the dispensation of the bone cement 322 from the device 100 takes place through a continued opposite rotation of the first container 200 with respect to the second container 300. In a further preferred embodiment, the vessel 210 is not fully destroyed after the dispensation of the bone cement 322. In a further preferred embodiment of the method 600, the vessel 210 is opened only in a spot after the dispensation of the bone cement 322.

It is an advantage of the method 600 according to one embodiment that the vessel 210 does not need to be destroyed completely while the bone cement 322 is being mixed and, optionally, dispensed. Firstly, this reduces the required expenditure of force by the user, secondly the disadvantages of fragments of the vessel 210 described above are prevented. It is another advantage of the method 600 according to one embodiment that the sub-steps 630 and 650 take place in sequence with similar process steps and that there is no possibility of changing or confusing the sequence of the process steps. Accordingly, the application of the method 600 is simple, safe, and rapid.

In summary, it can be noted that one embodiment is characterized by a device that includes two containers, whereby the monomer liquid is stored in the first container and the bone cement powder is stored in the second container. According to one embodiment, the first container is inserted into the second container, whereby the first container being inserted axially
1. opens the vessel for the monomer liquid;
2. conveys the monomer liquid into the bone cement powder; and
3. dispenses the ready-made bone cement produced from monomer liquid and bone cement powder without mixing, in the order given.

It is noted that the embodiments are described with reference to various states of facts. Specifically, some embodiments are described with reference to device claims, whereas other embodiments are described with reference to method claims. However, a person skilled in the art will interpret the aforementioned information and the description to understand, unless specified otherwise, that the present application discloses not only a combination of features belonging to one type of object, but also a combination of features relating to various objects. All features can be combined with each other, which may lead to synergy effects that exceed the simple sum of the effects of the features.

Whereas embodiments have been illustrated and described in detail in the drawings and the preceding description, the figures and descriptions shall be understood to be illustrative or exemplary and in no way as restrictive. The invention shall not be limited to the disclosed embodiments. Variations of the embodiments disclosed here can be comprehended and designed by persons skilled in the art from a study of the drawings, disclosure and independent claims.

The term "comprising" in the claims shall not exclude other elements or steps. Likewise, the indefinite article "a" or "an" shall not exclude any plurality. The mere fact of certain features being quoted in claims that are independent of each other shall not indicate that a combination of the claims could not be utilised to advantage. Any reference numbers in the claims shall not be interpreted as restrictions.

Although specific embodiments have been illustrated and described herein, it will be appreciated by those of ordinary skill in the art that a variety of alternate and/or equivalent implementations may be substituted for the specific embodiments illustrated and described without departing from the scope of the present embodiments. This application is intended to cover any adaptations or variations of the specific embodiments discussed herein. Therefore, it is intended that these embodiments be limited only by the claims and the equivalents thereof.

The invention claimed is:
1. A device for providing a bone cement made of two starting components, comprising:
   a hollow cylinder-shaped first container containing a glass ampoule with a monomer liquid as a first starting component and an opening device for the glass ampoule;
   a hollow cylinder-shaped second container comprising a container wall, a first internal space, and a second internal space;
   wherein a bone cement powder as a second starting component is stored in the first internal space; and wherein the monomer liquid can be conveyed into the second internal space;
a fluid-conducting conveying means arranged between the first internal space and the second internal space;
wherein the first container and the second container are axially connected to each other;
wherein a dispensing plunger is configured to be axially shifted in the second container and is arranged between the first container and the second internal space;
whereby the dispensing plunger acts in concert appropriately with the container wall such that,
in a first position of the dispensing plunger, the first container and the second internal space are connected in monomer liquid-conducting manner; and,
in a second position of the dispensing plunger, the first container and the second internal space are connected in monomer liquid-non-conducting manner so that the monomer liquid is conveyed into the first internal space.

2. The device of claim 1, wherein the container wall comprises a first subsection with at least one recess and a second subsection that is designed to be recess-free.

3. The device of claim 2, characterized in that the dispensing plunger, in the first position, is adjacent to the first subsection in appropriate manner such that the monomer liquid can flow about the dispensing plunger via the at least one recess.

4. The device of claim 2, characterized in that the dispensing plunger, in the second position, is adjacent to the second subsection in appropriate manner such that the monomer liquid cannot flow about the dispensing plunger.

5. The device of claim 1, characterized in that the dispensing plunger is cambered.

6. The device of claim 1, characterized in that the first container and the dispensing plunger are designed to be a single part.

7. The device of claim 1, characterized in that the opening device is a puncturing mandrel.

8. The device of claim 1, characterized in that the first container comprises an axially shiftable conveying plunger, designed appropriately such that the vessel can be conveyed onto the opening device by the conveying plunger.

9. The device of claim 1, characterized in that the first container can be inserted axially, at least in part, into the second container in appropriate manner such that the dispensing plunger can be moved over the length of the second internal space and at least a part of the length of the first internal space.

10. The device of claim 1, characterized in that the first container comprises an external thread and the second container comprises an internal thread, whereby the external thread and the internal thread are connected or can be connected to each other in form-fitting and/or force-locking manner.

* * * * *